United States Patent
Aires et al.

(10) Patent No.: US 9,248,083 B2
(45) Date of Patent: Feb. 2, 2016

(54) COSMETIC COMPOSITION COMPRISING AT LEAST ONE ORGANOSILICON COMPOUND, AT LEAST TWO ANIONIC SURFACTANTS AND AT LEAST ONE AMPHOTERIC SURFACTANT

(75) Inventors: Carine Aires, Paris (FR); Damien Drillon, Paris (FR); Valérie Viravau, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 12/977,458

(22) Filed: Dec. 23, 2010

(65) Prior Publication Data

US 2011/0182842 A1    Jul. 28, 2011

Related U.S. Application Data

(60) Provisional application No. 61/298,283, filed on Jan. 26, 2010.

(30) Foreign Application Priority Data

Dec. 23, 2009 (FR) .................................... 09 59486

(51) Int. Cl.
| | |
|---|---|
| *A61K 8/18* | (2006.01) |
| *A61K 8/39* | (2006.01) |
| *A61K 8/44* | (2006.01) |
| *A61K 8/46* | (2006.01) |
| *A61K 8/58* | (2006.01) |
| *A61Q 5/02* | (2006.01) |
| *A61Q 5/12* | (2006.01) |

(52) U.S. Cl.
CPC ... *A61K 8/39* (2013.01); *A61K 8/44* (2013.01); *A61K 8/442* (2013.01); *A61K 8/463* (2013.01); *A61K 8/466* (2013.01); *A61K 8/585* (2013.01); *A61Q 5/02* (2013.01); *A61Q 5/12* (2013.01)

(58) Field of Classification Search
CPC ........................................................ A61K 8/39
USPC ....................................................... 424/70.12
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,528,378 A | 10/1950 | Mannheimer | |
| 2,674,580 A | 4/1954 | Henkin | |
| 2,781,354 A | 2/1957 | Mannheimer | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,589,978 A | 6/1971 | Kamal et al. | |
| 3,632,559 A | 1/1972 | Matter et al. | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,031,307 A | 6/1977 | DeMartino et al. | |
| 4,075,136 A | 2/1978 | Schaper | |

(Continued)

FOREIGN PATENT DOCUMENTS

| | | |
|---|---|---|
| CA | 1069522 A1 | 1/1980 |
| EP | 0080976 A1 | 6/1983 |

(Continued)

OTHER PUBLICATIONS

French Search Report for FR 0959486, dated Sep. 7, 2010.

(Continued)

*Primary Examiner* — Jake Vu

(74) *Attorney, Agent, or Firm* — The Marbury Law Group, PLLC

(57) ABSTRACT

Provided herein is a cosmetic composition for washing and conditioning keratin fibers, comprising, in a cosmetically acceptable medium: (i) at least one organosilicon compound chosen from silanes comprising one silicon atom and siloxanes comprising two or three silicon atoms, wherein the at least one organosilicon compound also comprises at least one basic chemical functional group and at least one group chosen from hydroxyl and hydrolysable groups per molecule; (ii) at least one anionic surfactant chosen from sulfate and sulfonate anionic surfactants; (iii) at least one carboxylic anionic surfactant other than the at least one anionic surfactant of (ii) chosen from alkyl ether carboxylic acids and salts thereof, and (iv) at least one amphoteric surfactant. Also provided is a cosmetic process for treating keratin fibers, comprising applying the cosmetic composition to the keratin fibers.

9 Claims, No Drawings

(56) References Cited

U.S. PATENT DOCUMENTS

| | | | |
|---|---|---|---|
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,185,087 A | 1/1980 | Morlino | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,472,297 A | 9/1984 | Bolich et al. | |
| 4,579,732 A | 4/1986 | Grollier et al. | |
| 4,591,610 A | 5/1986 | Grollier | |
| 4,608,250 A | 8/1986 | Jacquet et al. | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,761,273 A | 8/1988 | Grollier et al. | |
| 4,777,040 A | 10/1988 | Grollier et al. | |
| 4,839,166 A | 6/1989 | Grollier et al. | |
| 4,948,579 A | 8/1990 | Jacquet et al. | |
| 4,970,066 A | 11/1990 | Grollier et al. | |
| 4,996,059 A | 2/1991 | Grollier et al. | |
| 5,009,880 A | 4/1991 | Grollier et al. | |
| 5,089,252 A | 2/1992 | Grollier et al. | |
| 5,196,189 A | 3/1993 | Jacquet et al. | |
| 5,958,392 A | 9/1999 | Grollier et al. | |
| 6,923,954 B2 | 8/2005 | Doi et al. | |
| 8,246,941 B2 * | 8/2012 | Decoster et al. | 424/70.24 |
| 8,435,501 B2 | 5/2013 | Peffly et al. | |
| 8,545,828 B1 | 10/2013 | Cao et al. | |
| 2006/0019844 A1 | 1/2006 | Aubrun-Sonneville et al. | |
| 2006/0233733 A1 | 10/2006 | Beauquey et al. | |
| 2006/0275245 A1 | 12/2006 | Decoster et al. | |
| 2009/0293899 A1 | 12/2009 | Woodland et al. | |
| 2011/0212044 A1 | 9/2011 | Kohno et al. | |

FOREIGN PATENT DOCUMENTS

| | | | | |
|---|---|---|---|---|
| EP | 0095238 | A2 | 11/1983 | |
| EP | 0122324 | A1 | 10/1984 | |
| EP | 0337354 | A1 | 10/1989 | |
| EP | 0530974 | A1 | 3/1993 | |
| EP | 1 726 293 | | 11/2006 | |
| EP | 1726293 | A1 | 11/2006 | |
| EP | 2248511 | A1 | 11/2010 | |
| FR | 1492597 | A | 8/1967 | |
| FR | 1583363 | A | 10/1969 | |
| FR | 2077143 | | 10/1971 | |
| FR | 2080759 | A | 11/1971 | |
| FR | 2162025 | A1 | 7/1973 | |
| FR | 2190406 | A2 | 2/1974 | |
| FR | 2252840 | A1 | 6/1975 | |
| FR | 2270846 | A1 | 12/1975 | |
| FR | 2280361 | A2 | 2/1976 | |
| FR | 2316271 | A1 | 1/1977 | |
| FR | 2320330 | A1 | 3/1977 | |
| FR | 2336434 | A1 | 7/1977 | |
| FR | 2368508 | A2 | 5/1978 | |
| FR | 2383660 | A1 | 10/1978 | |
| FR | 2393573 | A1 | 1/1979 | |
| FR | 2413907 | A1 | 8/1979 | |
| FR | 2470596 | A1 | 6/1981 | |
| FR | 2505348 | A1 | 11/1982 | |
| FR | 2519863 | A1 | 7/1983 | |
| FR | 2542997 | A1 | 9/1984 | |
| FR | 2598611 | A1 | 11/1987 | |
| FR | 2 789 896 | | 8/2000 | |
| FR | 2789896 | A1 | 8/2000 | |
| FR | 2910276 | A1 | 6/2008 | |
| FR | 2930439 | A1 | 10/2009 | |
| GB | 1546809 | A | 5/1979 | |
| GB | 2398240 | A | 8/2004 | |
| JP | 62-136235 | U | 8/1987 | |
| JP | 2001-323297 | A | 11/2001 | |
| WO | WO 00/48557 | * | 8/2000 | A61K 7/06 |
| WO | 2009/043841 | A2 | 4/2009 | |

OTHER PUBLICATIONS

English language abstract of FR 2 789 896, Aug. 25, 2000.
Porter, M.R., "Handbook of Surfactants," published by Blackie & Son (Glasgow and London), 1991, pp. 116-178.
Co-pending U.S. Appl. No. 12/977,116; Inventors: Valerie Viravau et al., "Cosmetic Composition Comprising at Least One Organosilicon Compound, at Least One Anionic Surfactant and at Least One Cationic Polymer," filed Dec. 23, 2010.
Non-Final Office Action for co-pending U.S. Appl. No. 12/977,116, dated Nov. 7, 2012.
Final Office Action for co-pending U.S. Appl. No. 12/977,116, dated Sep. 13, 2013.
French Search Report for FR 0959498, dated Sep. 7, 2010.
Co-pending U.S. Appl. No. 12/977,117; Inventors: Valerie Viravau et al., "Cosmetic Composition Comprising at Least One Organosilicon Compound, at Least One Anionic Surfactant and at Least One Nonionic Thickener, and Process Using the Composition," filed Dec. 23, 2010.
Non-Final Office Action for co-pending U.S. Appl. No. 12/977,117, dated Jan. 11, 2013.
Final Office Action for co-pending U.S. Appl. No. 12/977,117, dated Jul. 30, 2013.
Stearyl alcohol data from Kao Chemicals Europe (http://www.kaochemicals-eu.com/stearyl-alcohol-0, 1 page, accessed on Jul. 21, 2013).
Cetaryl alcohol data from Kao Chemicals Europe (http://www.kaochemicals-eu.com/cetearyl-alcohol-1, 1 page accessed on Jul. 21, 2013).
French Search Report for FR 0959497, dated Sep. 7, 2010.
Fonnum, G. et al., "Associative Thickeners. Part I: Synthesis, Rheology and Aggregation Behavior," Colloid & Polymer Science, 271, (1993), pp. 380-389.
MacGregor, E.A. et al., "Polymers in Nature," John Wiley & Sons, Chapter 6, 1980, pp. 240-328.
Kirk-Othmer's Encyclopedia of Chemical Technology, 3rd Edition, vol. 3, 1982, pp. 896-900.
Kirk-Othmer's Encyclopedia of Chemical Technology, 3rd Edition, vol. 15, 1982, pp. 439-458.
English language Abstract for JP 2001-323297 A (Nov. 22, 2001).
English language Abstract for FR 2910276 A1 (Jun. 27, 2008).
Final Office Action for Co-Pending U.S. Appl. No. 12/977,117, Dated Jun. 4, 2014.
Final Office Action for Co-Pending U.S. Appl. No. 12/977,117, Dated Feb. 25, 2014.
Non-Final Office Action for Co-Pending U.S. Appl. No. 12/977,116, Dated Jan. 9, 2015.
Non-Final Office Action for Co-Pending U.S. Appl. No. 12/977,116, Dated Jun. 18, 2014.

* cited by examiner

COSMETIC COMPOSITION COMPRISING AT LEAST ONE ORGANOSILICON COMPOUND, AT LEAST TWO ANIONIC SURFACTANTS AND AT LEAST ONE AMPHOTERIC SURFACTANT

This application claims benefit of U.S. Provisional Application No. 61/298,283, filed Jan. 26, 2010. This application also claims benefit of priority under 35 U.S.C. §119 to French Patent Application No. 0959486, filed Dec. 23, 2009.

Disclosed herein is a cosmetic composition for cleansing and conditioning keratin fibres, for example human keratin fibers such as the hair, comprising, in a cosmetically acceptable medium, at least one organosilicon compound, at least one anionic surfactant chosen from sulfate and sulfonate anionic surfactants, at least one carboxylic anionic surfactant and at least one amphoteric surfactant. Also disclosed herein is a cosmetic process for treating keratin fibres employing the cosmetic composition.

It may be common practice to use detergent compositions (such as shampoos) based, for example, on standard surfactants such as anionic, nonionic and/or amphoteric type, further such as anionic type, for cleansing and/or washing keratin materials such as the hair. These compositions can be applied to wet hair and the lather generated by massaging or frictioning with the hands makes it possible, after rinsing with water, to remove the diverse types of soiling initially present on the hair or the skin.

These detergent compositions can have good washing power, but their intrinsic cosmetic properties however may remain quite poor, for example, due to the fact that the relatively aggressive nature of such a cleansing treatment may in the long term give rise to more or less pronounced damage on hair fibers, associated, for example, with the gradual removal of the fats or proteins contained in or at their surface.

Thus, to improve the cosmetic properties of the above detergent compositions, and, for example, of those that can be applied to sensitized hair (i.e. hair that may be damaged or embrittled by the action of external atmospheric agents such as light and/or bad weather, and/or mechanical or chemical treatments such as blow-drying, combing, dyeing, bleaching, permanent-waving and/or relaxing), it may now become common practice to introduce into these compositions at least one additional cosmetic agent known as conditioning agent, which may be intended mainly to repair or limit the harmful or undesirable effects caused by the various treatments and/or attacking factors to which the hair fibers may be more or less repeatedly subjected. The at least one conditioning agent may, of course, also improve the cosmetic behaviour of natural hair.

With this aim, it may have already been proposed to use cosmetically active organic compounds such as cationic polymers and silicones as conditioning agents in detergent cosmetic compositions such as shampoos, to give the hair at least one satisfactory cosmetic property, for example, chosen from improved sheen, softness, suppleness, lightness, a natural feel and improved disentangling.

However, those compounds in cosmetic washing and hair-conditioning compositions may not give the hair satisfactory and/or long-lasting styling properties. For example, these compositions may generally afford styling effects, such as hair hold, body and/or manageability effects, which may remain insufficient and which may have a tendency to fade out after washing the hair with a standard shampoo.

Now, it can be found that consumers may be increasingly in search of washing compositions that can be not only capable of appropriately conditioning the hair, but also capable of affording satisfactory and long-lasting styling effects.

Thus, compositions for washing and conditioning the hair that comprise at least one organosilicon compound, such as 3-aminopropyltriethoxysilane, may have been developed in order to be able to satisfy these requirements. These washing compositions may make it possible to condition the hair, such as by giving it a satisfactory soft feel, while at the same time imparting pronounced and long-lasting styling effects.

Furthermore, these compositions can be beneficial since they may facilitate the shaping of fine hair and may give beneficial styling effects to wavy or curly hair, for example, by improving the fashioning and control of the curls.

However, washing compositions comprising such organosilicon compounds may have the drawback of changing substantially over time under normal storage conditions as a function of the temperature, for example, in terms of their viscosity and/or their visual aspect. In other words, these compositions may not be stable, which can be reflected by a cloudy visual aspect and/or by an unsatisfactory texture on storage.

For example, it has been found that organosilicon compounds, such as 3-aminopropyltriethoxysilane, can be chemically incompatible with essentially all the surfactants, such as anionic surfactants, which may be present in washing compositions, leading to the stability problems encountered.

Moreover, it may have been observed that the introduction of certain organosilicon compounds, for example, amino derivatives such as 3-aminopropyl-triethoxysilane, into washing compositions that, for example, have a pH ranging from 4 to 7, may also give rise to stability problems due to the alkaline nature of these compounds.

It can be beneficial to develop cosmetic compositions for cleansing and conditioning keratin fibers, comprising at least one organosilicon compound, wherein these compositions do not have at least one of the drawbacks described above, e.g. being stable over time and/or allowing hair to be conditioned satisfactorily while at the same time affording long-lasting, and/or powerful styling effects, for example, in terms of volume, body and/or texturizing of the hair.

Provided herein are detergent and conditioning compositions for keratin fibres, which can have at least one of the beneficial properties discussed above, comprising at least one organosilicon compound as defined hereinbelow, at least one anionic surfactant chosen from sulfate and sulfonate anionic surfactants, at least one carboxylic anionic surfactant different from the preceding ones, chosen from alkyl ether carboxylic acids and salts thereof, and at least one amphoteric surfactant.

For example, the use of at least one amphoteric surfactant and of at least one carboxylic anionic surfactant chosen from alkyl ether carboxylic acids and salts thereof, in cosmetic compositions comprising at least one organosilicon compounds and at least one anionic surfactants chosen from sulfate and sulfonate anionic surfactants, can make it possible to render them stable on storage both at room temperature (20-25° C.) and at 45° C., for example, in terms of their visual aspect and/or their viscosity.

As disclosed herein, the term "stable" means that the visual aspect and/or viscosity of these compositions do not change substantially over time under storage test conditions, for example at room temperature (20° C.-25° C.) and/or at 45° C. and/or at 4° C. for two months following their manufacture.

Furthermore, the compositions disclosed herein may lead to satisfactory treatment of the hair, thus giving it a satisfactory soft feel, improved disentangling, softness and/or suppleness.

Moreover, the compositions disclosed herein may afford powerful styling effects, for example, in terms of their provision of volume, body and/or manageability, and/or do so in a lasting manner.

Furthermore, the compositions disclosed herein may facilitate the shaping of the hair, for example, of fine hair, and/or may give improved styling effects to curly hair, for example, in terms of the fashioning and/or control of the curls, and/or do so in a lasting manner.

Provided herein is a cosmetic composition for washing and conditioning keratin fibres, for example, human keratin fibers such as the hair, comprising, in a cosmetically acceptable medium:

(i) at least one organosilicon compound chosen from silanes comprising one silicon atom and siloxanes comprising two or three silicon atoms, wherein the at least one organosilicon compound comprises at least one basic chemical functional group and at least one group chosen from hydroxyl and hydrolysable groups per molecule;

(ii) at least one anionic surfactant chosen from sulfate and sulfonate anionic surfactants, (iii) at least one carboxylic anionic surfactant other than the at least one anionic surfactant of (ii), chosen from alkyl ether carboxylic acids and salts thereof, and (iv) at least one amphoteric surfactant.

Also provided is a cosmetic process for treating keratin fibers, such as for washing and conditioning the hair, comprising applying the cosmetic compositions disclosed herein to the keratin fibers.

Other subjects and characteristics, aspects and benefits of the present disclosure will emerge even more clearly on reading the description and the example that follows.

The at least one organosilicon compound disclosed herein can be chosen from organosilanes comprising at least one silicon atom and organosiloxanes comprising at least two silicon atoms, such as two silicon atoms. The at least one organosilicon compound can also comprise at least one basic chemical functional group, such as only one basic chemical functional group. The at least one basic chemical functional group may correspond to any functional group that can give the at least one organosilicon compound a basic nature, for example an amine group such as a primary, secondary or tertiary amine group. The at least one organosilicon compound disclosed herein may optionally comprise at least one additional functional groups, for instance, chosen from acid functional groups and halogen.

The at least one organosilicon compound disclose herein may also comprise at least one group chosen from hydrolysable and hydroxyl groups per molecule. The hydrolysable groups can be, for example, chosen from alkoxy, aryloxy and halogen.

According to at least one embodiment, the at least one organosilicon compound disclosed herein is chosen from silanes of formula (I):

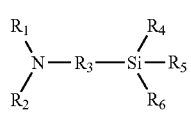
(I)

in which:
$R_4$ represents a halogen, OR', or $R'_1$;
$R_5$ represents a halogen, OR", or $R'_2$;
$R_6$ represents a halogen, OR''', or $R'_3$;

$R_1$, $R_2$, R', R", and R''' represent, independently of each other, hydrogen, a saturated or unsaturated, linear or branched hydrocarbon-based group optionally bearing at least one additional chemical group;

$R_3$, $R'_1$, $R'_2$ and $R'_3$ represent, independently of each other, a saturated or unsaturated, linear or branched hydrocarbon-based group optionally bearing at least one additional chemical group;

Provided at least two of the groups $R_4$, $R_5$ and $R_6$ respectively represent OR', OR" and OR''', and at least two of the groups R', R" and R''' are not hydrogen.

According to at least one embodiment, $R_1$, $R_2$, R', $R'_1$, $R'_2$, $R'_3$, R" and R''', independently of each other, are chosen from $C_1$-$C_{12}$ alkyl, $C_6$-$C_{14}$ aryl, $(C_1$-$C_8)$alkyl$(C_6$-$C_{14})$aryl, and $(C_6$-$C_{14})$aryl$(C_1$-$C_8)$alkyl radicals.

According to at least one embodiment, the at least one organosilicon compound is chosen from siloxanes of formula (II):

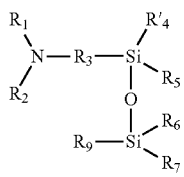
(II)

in which:
$R_1$, $R_2$, $R_3$, $R_5$ and $R_6$ are as defined previously;
$R'_4$ represents a halogen or $OR_{11}$;
$R_7$ represents a halogen, $OR_{10}$, or $R''_1$;
$R_9$ represents a halogen, $OR_8$, $R''_2$, or $R_3NR_1R_2$;
$R_8$, $R_{10}$ and $R_{11}$ represent, independently of each other, hydrogen, a saturated or unsaturated, linear or branched hydrocarbon-based group, optionally bearing at least one additional chemical group;
$R''_1$, $R''_2$ represent, independently of each other, a saturated or unsaturated, linear or branched hydrocarbon-based group, optionally bearing at least one additional chemical group;
Provided that at least one of $R_6$, $R_7$ and $R_9$ represents a halogen, OR''', $OR_{10}$, or $OR_8$.

According to at least one embodiment, $R''_1$, $R''_2$, $R_8$ or $R_{10}$ and $R_{11}$, independently of each other, are chosen from $C_1$-$C_{12}$ alkyl, $C_6$-$C_{14}$ aryl, $(C_1$-$C_8)$alkyl$(C_6$-$C_{14})$aryl, and $(C_6$-$C_{14})$aryl$(C_1$-$C_8)$alkyl radicals.

According to at least one embodiment, the halogen is chlorine.

The at least one organosilicon compound as disclosed herein is, for example, chosen from organosilanes of formula (III):

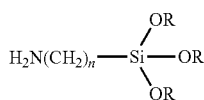
(III)

in which the radicals R, which may be identical or different, are chosen from $C_1$-$C_6$ and for example $C_1$-$C_2$ alkyl radicals, and n is an integer ranging from 1 to 6 and such as from 2 to 4.

According to at least one embodiment, the at least one silane and/or siloxane are water-soluble and for example are soluble to a concentration of 2%, for further example to a concentration of 5% and for even further example to a concentration of 10% by weight in water at a temperature of 25° C.±5° C. and at atmospheric pressure. As disclosed herein, the term "soluble" means the formation of a single macroscopic phase.

According to at least one embodiment, the at least one organosilicon compound present in the composition disclosed herein is 3-aminopropyltriethoxysilane.

The at least one organosilicon compound may be present in the composition disclosed herein in a total amount ranging from 0.01% to 10% by weight, such as ranging from 0.1% to 5% by weight and further such as ranging from 0.2% to 2% by weight relative to the total weight of the composition.

As indicated previously, the cosmetic composition disclosed herein also comprises at least one anionic surfactant chosen from sulfate and sulfonate anionic surfactants.

The at least one sulfate or sulfonate anionic surfactant disclosed herein can be an anionic surfactant comprising at least one or more sulfate functional group ($-OSO_3H$ or $-OSO_3^-$) or at least one sulfonate functional group ($-SO_3H$ or $-SO_3^-$), respectively.

The at least one anionic surfactant chosen from sulfate and sulfonate anionic surfactants, in the context of the present disclosure can be chosen from the salts (for example alkali metal salts, such as of sodium, ammonium salts, amine salts, amino alcohol salts or magnesium salts) of alkyl sulfates, alkylamide sulfates, alkyl ether sulfates, alkylamide ether sulfates, alkylaryl ether sulfates, alkyl ether sulfosuccinates, acyl isethionates and methyl acyl taurates; the alkyl or acyl radical of all these various compounds, for example, comprising from 8 to 24 carbon atoms, and the aryl radical, for example, representing a phenyl or benzyl group.

The mean number of ethylene oxide or propylene oxide groups may range, for example, from 2 to 50, for further example, from 2 to 10 and for even further example, from 2 to 5.

According to at least one embodiment, the cosmetic composition disclosed herein comprises at least one anionic surfactant chosen from sodium, triethanolamine, magnesium and ammonium ($C_{12}$-$C_{14}$)alkyl sulfates, oxyethylenated sodium, ammonium and magnesium ($C_{12}$-$C_{14}$)alkyl ether sulfates, sodium cocoyl isethionate and methyl acyl taurates.

According to at least one embodiment, the at least one anionic surfactant chosen from sulfate and sulfonate anionic surfactants can be chosen from sodium ($C_{12}$-$C_{14}$)alkyl ether sulfates, such as sodium lauryl ether sulfate, and further such as those comprising from 2 to 3 mol of ethylene oxide.

The at least one anionic surfactant chosen from sulfate and sulfonate anionic surfactants can be present in a total amount ranging from 1% to 25% by weight, such as in a total amount ranging from 3% to 20% by weight and further such as in a total amount ranging from 5% to 15% by weight relative to the total weight of the cosmetic composition.

The cosmetic composition also comprises at least one carboxylic anionic surfactant other than the at least one surfactant of (ii), which can be chosen from alkyl ether carboxylic acids and salts thereof.

The at least one carboxylic anionic surfactant other than the at least one anionic surfactant of (ii), for example, does not comprise any sulfate or sulfonate functional groups and can be chosen from polyoxyalkylenated ($C_6$-$C_{24}$)alkyl ether carboxylic acids and salts thereof, for example, those comprising from 2 to 50 alkylene oxide and for further example those comprising ethylene oxide groups, such as the compounds sold by the company Kao under the name AKYPO.

The salts can be chosen for example from alkali metal salts, such as sodium salts, ammonium salts, amine salts, salts of amino alcohols such as triethanolamine and monoethanolamine, and magnesium salts.

The at least one carboxylic anionic surfactant of (iii) can be, for example, chosen from compounds of formula (IV) below:

$$R_1-(OC_2H_4)_n-OCH_2COOA \qquad (IV)$$

in which:

$R_1$ represents a linear or branched $C_8$-$C_{22}$ alkyl or alkenyl radical, a ($C_8$-$C_9$)alkylaryl radical, a $R_2CONH-CH_2-CH_2-$ radical with $R_2$ representing a linear or branched $C_{11}$-$C_{21}$ alkyl or alkenyl radical, n is an integer or decimal number (average value) ranging from 2 to 24 and such as from 2 to 10, and as further examples, the alkyl radical can comprise from 8 to 20 carbon atoms, and the aryl can be phenyl, A represents a hydrogen, an ammonium cation, $Na^+$, $K^+$, $Li^+$, $Mg^+$ or a monoethanolamine or triethanolamine cation, such as a hydrogen or $Na^+$, further such as $Na^+$.

According to at least one embodiment, $R_1$ represents a linear or branched $C_8$-$C_{22}$ alkyl or alkenyl radical, or a ($C_8$-$C_9$)alkylphenyl radical.

The at least one carboxylic anionic surfactant of (iii) or salts thereof disclosed herein are for example chosen from those of formula (IV) in which $R_1$ represents a ($C_{12}$-$C_{14}$) alkyl, cocoyl, or oleyl radical; a nonylphenyl or octylphenyl radical, A represents a hydrogen or $Na^+$, and n ranges from 2 to 20 and such as from 2 to 10.

According to at least one embodiment, the at least one carboxylic anionic surfactant of (iii) can be chosen from compounds of formula (IV) in which $R_1$ represents a $C_{12}$-$C_{14}$ and such as a $C_{12}$ alkyl radical, A represents a hydrogen or $Na^+$, such as $Na^+$, and n ranges from 2 to 10.

Among the commercial products that may be used non-limiting mention may be made of the products sold by the company Chem Y under the names:

AKYPO NP 70 (R=nonylphenyl, n=7, A=H);
AKYPO NP 40 (R=nonylphenyl, n=4, A=H);
AKYPO OP 40 (R=octylphenyl, n=4, A=H);
AKYPO OP 80 (R=octylphenyl, n=8, A=H);
AKYPO OP 190 (R=octylphenyl, n=19, A=H);
AKYPO RLM 38 (R=($C_{12}$-$C_{14}$)alkyl, n=3.8 and A=H);
AKYPO RLM 38 NV (R=($C_{12}$-$C_{14}$)alkyl, n=4, A=$Na^+$);
AKYPO RLM 45 (R=($C_{12}$-$C_{14}$)alkyl, n=4.5 and A=H);
AKYPO RLM 45 NV (R=($C_{12}$-$C_{14}$)alkyl, n=4.5, and A=$Na^+$);
AKYPO RLM 100 (R=($C_{12}$-$C_{14}$)alkyl, n=10, and A=H);
AKYPO RLM 100 NV (R=($C_{12}$-$C_{14}$)alkyl, n=10, and A=$Na^+$);
AKYPO RLM 130 (R=($C_{12}$-$C_{14}$)alkyl, n=13, and A=H);
AKYPO RLM 160 NV (R=($C_{12}$-$C_{14}$)alkyl, n=16, and A=$Na^+$);
or by the company Sandoz under the names:
SANDOPAN DTC-Acid (R=($C_{13}$)alkyl, n=6, and A=H);
SANDOPAN DTC (R=($C_{13}$)alkyl, n=6, and A=$Na^+$);
SANDOPAN LS 24 (R=($C_{12}$-$C_{14}$)alkyl, n=12, and A=$Na^+$);
SANDOPAN JA 36 (R=($C_{13}$)alkyl, n=18, and A=H),
and such as the products sold under the following names:
AKYPO RLM 45;
AKYPO RLM 100;
AKYPO RLM 38.

According to at least one embodiment, the at least one carboxylic anionic surfactant of (iii) disclosed herein can be the product sold under the name AKYPO RLM 45.

The at least one carboxylic anionic surfactant of (iii) can be present in a total amount ranging from 0.05% to 10% by weight, such as in a total amount ranging from 0.1% to 8% by weight and further such as in a total amount ranging from 0.2% to 5% by weight relative to the total weight of the composition.

As indicated previously, the cosmetic composition disclosed herein also comprises at least one amphoteric surfactant.

The at least one amphoteric or zwitterionic surfactant used in the cosmetic composition disclosed herein may be, for example, chosen from secondary and tertiary aliphatic amine derivatives in which the aliphatic group is a linear or branched chain comprising from 8 to 22 carbon atoms and comprising at least one anionic group, for instance a carboxylate, sulfonate, sulfate, phosphate or phosphonate group. Mention may be made, for example, of ($C_8$-$C_{20}$)alkylbetaines, sulfobetaines, ($C_8$-$C_{20}$)alkylamido($C_6$-$C_8$)alkylbetaines or ($C_8$-$C_{20}$)alkylamido($C_6$-$C_8$)alkylsulfobetaines.

Among the amine derivatives, exemplary mention may be made of the products sold under the name MIRANOL®, as described in U.S. Pat. No. 2,528,378 and U.S. Pat. No. 2,781,354 and classified in the CTFA dictionary, 3rd edition, 1982, under the names Amphocarboxyglycinate and Amphocarboxypropionate, having the respective structures (V) and (VI):

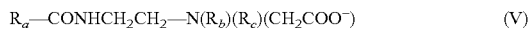

$$R_a\text{—CONHCH}_2\text{CH}_2\text{—N}(R_b)(R_c)(\text{CH}_2\text{COO}^-) \quad (V)$$

in which:
$R_a$ represents the alkyl group from an acid $R_a$—COOH present in hydrolyzed coconut oil, a heptyl, nonyl or undecyl group,
$R_b$ represents a β-hydroxyethyl group, and
$R_c$ represents a carboxymethyl group;
and

$$R_a'\text{—CONHCH}_2\text{CH}_2\text{—N(B)(B')} \quad (VI)$$

in which:
B represents —$CH_2CH_2OX'$,
B' represents —$(CH_2)_z$—Y', with z=1 or 2,
X' represents a —$CH_2CH_2$—COOH group or a hydrogen,
Y' represents —COOH or a —$CH_2$—CHOH—$SO_3H$ group,
$R_a'$ represents the alkyl group from acid $R_a'$—COOH present in coconut oil or in hydrolysed linseed oil, such as a $C_{17}$ alkyl group and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, or cocoamphodipropionic acid.

By way of example, mention may be made of the cocoamphodiacetate sold by the company Rhodia under the trade name MIRANOL® C2M Concentrate.

The at least one amphoteric or zwitterionic surfactant may be, for example, chosen from ($C_{8-20}$ alkyl)betaines and ($C_{8-20}$ alkyl)amido($C_{6-8}$ alkyl)betaines.

The at least one amphoteric surfactant may be present in a total amount ranging from 0.1% to 15% by weight, such as in a total amount ranging from 0.5% to 10% by weight and further such as in a total amount ranging from 1% to 8% by weight relative to the total weight of the cosmetic composition disclosed herein.

The cosmetic composition disclosed herein may further comprise at least one additional surfactant chosen from nonionic surfactants.

Examples of additional nonionic surfactants that may be used in the compositions disclosed herein are described, for example, in the *Handbook of Surfactants* by M. R. Porter, published by Blackie & Son (Glasgow and London), 1991, pp. 116-178. They can be chosen for example from polyethoxylated, polypropoxylated and polyglycerolated fatty acids, ($C_1$-$C_{20}$)alkylphenols, α-diols and alcohols, having a fatty chain comprising, for example, 8 to 18 carbon atoms, the number of ethylene oxide or propylene oxide groups possibly ranging for example from 2 to 50 and the number of glycerol groups possibly ranging for example from 2 to 30.

Exemplary mention may also be made of condensates of ethylene oxide and/or of propylene oxide with fatty alcohols; polyethoxylated fatty amides for example having from 2 to 30 ethylene oxide units, polyglycerolated fatty amides comprising on average from 1 to 5, and such as from 1.5 to 4, glycerol groups, ethoxy related fatty acid esters of sorbitan comprising from 2 to 30 ethylene oxide units, fatty acid esters of sucrose, fatty acid esters of polyethylene glycol, ($C_{6-24}$ alkyl)polyglycosides, N—($C_{6-24}$ alkyl)glucamine derivatives, amine oxides such as ($C_{10}$-$C_{14}$)alkylamine oxides or N—($C_{10-14}$ acyl)aminopropyl-morpholine oxides.

The at least one additional nonionic surfactant may be present in the compositions disclosed herein in a total amount ranging from 0.01% to 10% by weight and such as from 0.1% to 10% by weight relative to the total weight of the composition.

According to at least one embodiment, the total amount of the surfactants in the cosmetic composition disclosed herein may range from 3% to 50% by weight, such as from 5% to 30% by weight and further such as from 8% to 20% by weight relative to the total weight of the cosmetic composition.

The cosmetic composition may also comprise at least one cationic polymer.

As disclosed herein, the term "cationic polymer" means any polymer comprising at least one cationic group and/or at least one group that may be ionized into a cationic group.

The at least one cationic polymer that may be present in the composition disclosed herein may be chosen from those already known for improving the cosmetic properties of the hair, e.g. for example, those described in patent application EP-A-337 354 and in French patents FR-2 270 846, 2 383 660, 2 598 611, 2 470 596 and 2 519 863.

The at least one cationic polymer can be chosen, for example, from those comprising at least one primary, secondary, tertiary and/or quaternary amine group, which may either form part of the main polymer chain or be borne by a side substituent directly attached thereto.

The at least one cationic polymer may, for example, have a number-average molecular mass ranging from 500 to $5\times10^6$ and such as from $10^3$ to $3\times10^6$.

Among the cationic polymers that may be mentioned are, for example, polymers of the polyamine, polyamino amide and polyquaternary ammonium type.

These are known products. They are described, for example, in French patents 2 505 348 and 2 542 997. Among the polymers, exemplary mention may be made of:

(1) Homopolymers or copolymers derived from acrylic or methacrylic esters or amides and comprising at least one unit chosen from formula (VII), (VIII), (IX) and (X) below:

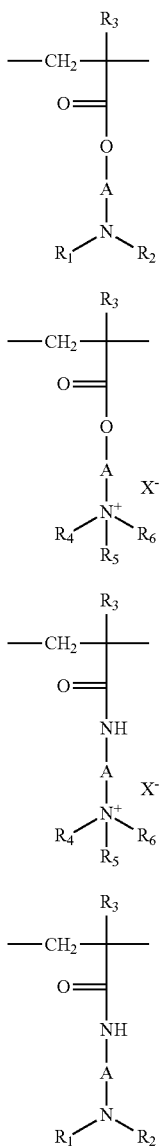

in which:

R<sub>3</sub>, which may be identical or different, represents a hydrogen or a CH<sub>3</sub> radical;

A, which may be identical or different, represents a linear or branched alkyl group comprising from 1 to 6 carbon atoms, such as 2 or 3 carbon atoms, or a hydroxyalkyl group comprising from 1 to 4 carbon atoms;

$R_4$, $R_5$ and $R_6$, which may be identical or different, represent an alkyl group comprising from 1 to 18 carbon atoms such as an alkyl group comprising from 1 to 6 carbon atoms, or a benzyl radical;

$R_1$ and $R_2$, which may be identical or different, represent hydrogen or an alkyl group comprising from 1 to 6 carbon atoms, such as methyl or ethyl;

$X^-$ represents an anion derived from an inorganic or organic acid, such as a methosulfate anion or a halide such as chloride or bromide.

Mention may be made, for example, of ethyltrimethylammonium methacrylate chloride homopolymer.

The polymers of family (1) can also comprise at least one unit derived from comonomers which may be chosen from the family of acrylamides, methacrylamides, diacetone acrylamides, acrylamides and methacrylamides substituted on the nitrogen with lower ($C_1$-$C_4$) alkyls, acrylic and methacrylic acids and esters thereof, vinyllactams such as vinylpyrrolidone and vinylcaprolactam, and vinyl esters.

Thus, among these polymers of family (1), exemplary mention may be made of:

copolymers of acrylamide and of dimethylaminoethyl methacrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in patent application EP-A-080 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or methacrylate copolymers, such as the products sold under the name GAFQUAT by the company ISP, such as, for example, GAFQUAT 734 or GAFQUAT 755, or alternatively the products known as COPOLYMER 845, 958 and 937. These polymers are, for example, described in French patents 2 077 143 and 2 393 573, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyldimethylamine copolymers sold for example under the name STYLEZE CC 10 by ISP, and quaternized vinylpyrrolidone/dimethylaminopropylmethacrylamide copolymers such as the product sold under the name GAFQUAT HS 100 by the company ISP.

crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising at least one olefinic group, such as methylenebisacrylamide. A crosslinked acrylamide/methacryloyloxyethyltrimethylammonium chloride copolymer (20/80 by weight) in the form of a dispersion comprising 50% by weight of the copolymer in mineral oil, for example, can be used. This dispersion is sold, for example, under the name SALCARE® SC 92 by the company Ciba. A crosslinked methacryloyloxyethyltrimethylammonium chloride homopolymer comprising about 50% by weight of the homopolymer in mineral oil or in a liquid ester can also be used. These dispersions are sold, for example, under the names SALCARE® SC 95 and SALCARE® SC 96 by the company Ciba.

(2) The cellulose ether derivatives comprising quaternary ammonium groups, described, for example, in French patent 1 492 597, and such as polymers sold under the names UCARE POLYMER "JR" (JR 400, JR 125 and JR 30M) or "LR" (LR 400 or LR 30M) by the company Amerchol. These polymers are, for example, also defined in the CTFA dictionary as quaternary ammoniums of hydroxyethylcellulose that have reacted with an epoxide substituted with a trimethylammonium group.

(3) Cellulose copolymers or cellulose derivatives grafted with a water-soluble monomer of quaternary ammonium, and described, for example, in U.S. Pat. No. 4,131,576, such as hydroxyalkylcelluloses, for instance hydroxymethyl-, hydroxyethyl- or hydroxypropyl-celluloses grafted, for example, with a methacryloylethyltrimethylammonium, methacrylamidopropyltrimethylammonium and/or dimethyldiallylammonium salt.

The commercial products corresponding to this definition are for example the products sold under the names CELQUAT L 200 and CELQUAT H 100 by the company National Starch.

(4) The cationic guar gums described for example in U.S. Pat. Nos. 3,589,578 and 4,031,307, such as guar gums comprising cationic trialkylammonium groups. Guar gums modified with a salt (e.g. chloride) of 2,3-epoxypropyltrimethylammonium can be used, for example.

Such products are sold for example under the trade names JAGUAR C13 S, JAGUAR C 15, JAGUAR C 17 or J JAGUAR C162 by the company Rhodia.

(5) Polymers formed from piperazinyl units and divalent alkylene or hydroxyalkylene radicals comprising straight or branched chains, optionally interrupted with oxygen, sulfur and/or nitrogen atoms or with aromatic and/or heterocyclic rings, and also the oxidation and/or quaternization products of these polymers. Such polymers are described, for example, in French patents 2 162 025 and 2 280 361.

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, and/or a bis-alkyl halide, or alternatively with an oligomer resulting from the reaction of a difunctional compound with a bis-halohydrin, a bis-azetidinium, a bis-haloacyldiamine, a bis-alkyl halide, an epihalohydrin, a diepoxide and/or a bis-unsaturated derivative; the crosslinking agent being used in proportions ranging from 0.025 to 0.35 mol per amine group of the polyamino amide; these polyamino amides can be alkylated or, if they comprise at least one tertiary amine functional group, they can be quaternized. Such polymers are described, for example, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyl-dialkylenetriamine polymers in which the alkyl radical comprises from 1 to 4 carbon atoms and for example, represents methyl, ethyl or propyl. Such polymers are described for example in French patent 1 583 363.

Among these derivatives, mention may be made, for example, of the adipic acid/dimethylaminohydroxypropyl/diethylenetriamine polymers sold under the name CARTARETINE F, F4 or F8 by the company Sandoz.

(8) The polymers obtained by reaction of a polyalkylene polyamine comprising at least two primary amine groups and at least one secondary amine group with a dicarboxylic acid chosen from diglycolic acid and saturated aliphatic dicarboxylic acids comprising from 3 to 8 carbon atoms. The mole ratio of the polyalkylene polyamine to the dicarboxylic acid ranges from 0.8:1 to 1.4:1; the polyamino amide resulting therefrom can be reacted with epichlorohydrin in a mole ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Polymers of this type are sold for example under the name HERCOSETT 57 by the company Hercules Inc. or alternatively under the name PD 170 or DELSETTE 101 by the company Hercules in the case of the adipic acid/epoxypropyl/diethylenetriamine copolymer.

(9) Cyclopolymers of alkyldiallylamine or of dialkyldiallylammonium, such as the homopolymers or copolymers comprising, as main constituent of the chain, at least one unit chosen from those of formula (XI) and (XII):

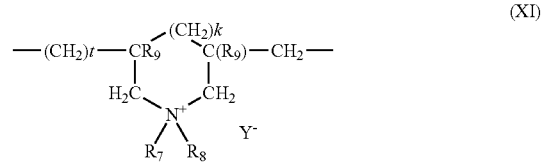

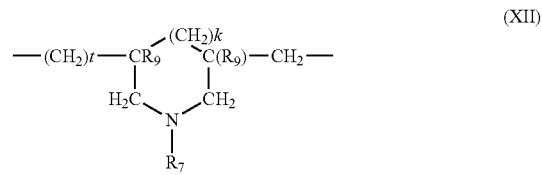

in which k and t are equal to 0 or 1, the sum k+t being equal to 1; $R_9$ represents hydrogen or a methyl radical; $R_7$ and $R_8$, independently of each other, represent an alkyl group comprising from 1 to 6 carbon atoms, a hydroxyalkyl group in which the alkyl group, for example, comprises from 1 to 5 carbon atoms, or a lower ($C_1$-$C_4$) amidoalkyl group, or $R_7$ and $R_8$ may represent, together with the nitrogen atom to which they are attached, heterocyclic groups, such as piperidyl or morpholinyl; or $R_7$ and $R_8$, independently of each other, for example, represent an alkyl group comprising from 1 to 4 carbon atoms; $Y^-$ is an anion such as bromide, chloride, acetate, borate, citrate, tartrate, bisulfate, bisulfite, sulfate or phosphate. These polymers are described, for example, in French patent 2 080 759 and in its Certificate of Addition 2 190 406.

Among the polymers defined above, mention may be made, for example, of the dimethyldiallylammonium chloride homopolymer sold under the name MERQUAT 100 by the company Nalco (and its homologues of low weight-average molecular mass) and the copolymers of diallyldimethylammonium chloride and of acrylamide, sold under the names MERQUAT 550 and MERQUAT 7SPR.

(10) The quaternary diammonium polymer comprising repeating units of formula (XIII):

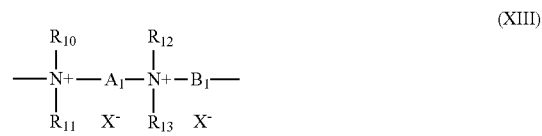

in which:

$R_{10}$, $R_{11}$, $R_{12}$ and $R_{13}$, which may be identical or different, represent aliphatic, alicyclic or arylaliphatic radicals comprising from 1 to 6 carbon atoms, or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally comprising a second heteroatom other than nitrogen, or alternatively $R_{10}$, $R_{11}$, $R_{12}$ and $R_{13}$ represent, independently of each other, a linear or branched $C_1$-$C_6$ alkyl radical optionally substituted with at least one group chosen from nitrile, ester, acyl, amide, —CO—O—$R_{14}$-D, and —CO—NH—$R_{14}$-D where $R_{14}$ is an alkylene and D is a quaternary ammonium group;

$A_1$ and $B_1$ represent, independently of each other, polymethylene groups comprising from 2 to 8 carbon atoms, which may be linear or branched, saturated or unsaturated, and which may comprise, linked to or intercalated in the main chain, at least one group chosen from aromatic ring, oxygen, sulfur, sulfoxide, sulfone, disulfide, amino, alkylamino, hydroxyl, quaternary ammonium, ureido, amide, and ester groups, and $X^-$ represents an anion derived from a mineral or organic acid;

$A_1$, $R_{10}$ and $R_{12}$ can form, with the two nitrogen atoms to which they are attached, a piperazine ring; in addition, if $A_1$ represents a linear or branched, saturated or unsaturated alkylene or hydroxyalkylene radical, $B_1$ can also represent —$(CH_2)_n$—CO-D-OC—$(CH_2)_n$— groups in which D represents:

a) a glycol residue of formula: —O—Z—O—, where Z represents a linear or branched hydrocarbon-based radical or a group corresponding to one of the following formulae:

—(CH$_2$—CH$_2$—O)$_x$—CH$_2$—CH$_2$—

—[CH$_2$—CH(CH$_3$)—O]$_y$—CH$_2$—CH(CH$_3$)— where x and y represent, independently of each other, an integer ranging from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y represents a linear or branched hydrocarbon-based radical, or alternatively the divalent radical

—CH$_2$—CH$_2$—S—S—CH$_2$—CH$_2$—;

d) a ureylene group of formula: —NH—CO—NH—.

According to at least one embodiment, $X^-$ is an anion such as chloride or bromide.

These polymers may, for example, have a number-average molecular mass ranging from 1000 to 100,000.

Polymers of this type are described, for example, in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is, for example, possible to use polymers that are formed from repeating units of formula (XIV):

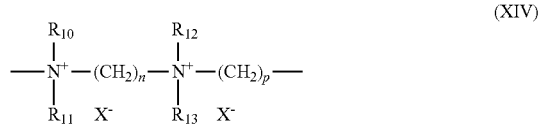

in which $R_{10}$, $R_{11}$, $R_{12}$ and $R_{13}$, which may be identical or different, represent an alkyl or hydroxyalkyl radical comprising from 1 to 4 carbon atoms, n and p are integers ranging from 2 to 8, and $X^-$ is an anion derived from a mineral or organic acid. Mention may be made, for example, of MEXOMER PO sold by the company Chimex.

(11) Polyquaternary ammonium polymers formed from repeating units of formula (XV):

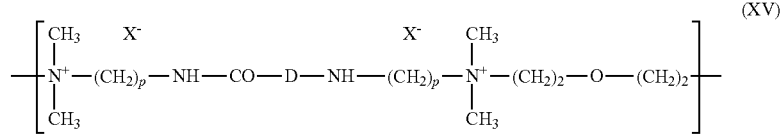

in which p represents an integer ranging from 1 to 6, D may be absent or may represent a group —$(CH_2)_r$—CO— in which r represents a number equal to 4 or 7, and $X^-$ is an anion.

Such polymers may be prepared according to the processes described, for example, in U.S. Pat. Nos. 4,157,388, 4,702,906 and 4,719,282. They are described for example in patent application EP-A-122 324.

Among these products, examples that may be mentioned include MIRAPOL A 15, MIRAPOL AD1, MIRAPOL AZ1 and MIRAPOL 175 sold by the company Miranol.

(12) Quaternary polymers of vinylpyrrolidone and of vinylimidazole, for instance the products sold under the names LUVIQUAT FC 905, FC 550 and FC 370 by the company BASF. These polymers may also comprise other monomers, for instance diallyldialkylammonium halides. Mention may be made, for example, of the product sold under the name LUVIQUAT SENSATION by the company BASF.

(13) Polyamines such as POLYQUART H sold by Henkel, which is given under the reference name Polyethylene glycol (15) Tallow Polyamine in the CTFA dictionary, or oxyethylenated (15 OE) coconut polyamines.

Other cationic polymers that may be used in the context of the disclosure are polyalkyleneimines, such as polyethyleneimines, polymers comprising vinylpyridine and/or vinylpyridinium units, condensates of polyamines and of epichlorohydrin, quaternary polyureylenes and chitin derivatives.

Among all the cationic polymers that may be used in the context of the present disclosure, exemplary mention may be made of polymers of families (1), (2), (3), (4), (10) and (12).

According to at least one embodiment, the at least one cationic polymer is chosen from cationic celluloses, cationic guar gums and quaternary polymers of vinylpyrrolidone and of vinylimidazole optionally combined with other monomers.

According to at least one embodiment, the at least one cationic polymer is chosen from hydroxyalkylcelluloses, such as hydroxymethyl-, hydroxyethyl- and hydroxypropylcelluloses grafted, for example, with a methacryloylethyltrimethylammonium, methylacrylamidopropyltrimethylammonium and/or dimethyldiallylammonium salt, cationic guar gums, and the copolymer of vinylpyrrolidone and vinylimidazole and dimethyldiallylammonium chloride.

The at least one cationic polymer may be present in the composition disclosed herein in a total amount ranging from 0.01% to 5% by weight relative to the total weight of the composition, such as from 0.1% to 1% by weight and further such as from 0.15% to 0.5% by weight relative to the total weight of the composition.

The cosmetic composition disclosed herein may also comprise at least one organic acid.

The term "organic acid" means any non-polymeric organic compound comprising at least one acid functional group chosen from carboxylic acid, sulfonic acid and phosphoric acid.

According to at least one embodiment, the at least one organic acid is not a surfactant.

According to at least one embodiment, the molecular weight of the at least one organic acid is less than 250 and such as less than 200.

The at least one organic acid may be an amino acid.

The at least one organic acid can be for example chosen from acetic acid, propanoic acid, butanoic acid, lactic acid, malic acid, glycolic acid, ascorbic acid, maleic acid, phthalic acid, succinic acid, taurine, tartaric acid, arginine, glycine, glucuronic acid, gluconic acid and citric acid.

According to at least one embodiment, the at least one organic acid according to the disclosure is chosen from carboxylic acids such as α-hydroxylated carboxylic acids, e.g., AHAs.

According to at least one embodiment, the at least one organic acid disclosed herein is acetic acid, citric acid or, for example, lactic acid.

In the composition, the at least one organic acid may be in free and/or salified form.

The at least one organic acid that may be used in the composition according to the present disclosure may be present in a total amount, expressed as free acids, ranging from 0.01% to 10% by weight, such as in a total amount ranging from 0.1% to 8% by weight and further such as in a total amount ranging from 0.2% to 5% by weight relative to the total weight of the composition.

The cosmetic composition disclosed herein may also comprise at least one silicone, such as amino silicone.

As disclosed herein, the term "amino silicone" means any silicone comprising at least one primary, secondary or tertiary amine function or a quaternary ammonium group.

The amino silicones that may be used in the cosmetic composition disclosed herein are chosen from:

(a) compounds of formula (XVI):

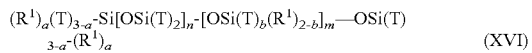

(XVI)

in which:

T is a hydrogen or a phenyl, hydroxyl (—OH) or $C_1$-$C_8$ alkyl radical, such as methyl, or a $C_1$-$C_8$ alkoxy, such as methoxy, a represents an integer ranging from 0 to 3, and according to at least one embodiment, a is 0, b represents 0 or 1, and for example, b represents 1, m and n are numbers such that the sum (n+m) can range, for example, from 1 to 2000 and further for example from 50 to 150, n may represent a number ranging from 0 to 1999 and such as from 49 to 149, and m may represent a number ranging from 1 to 2000 and such as from 1 to 10;

$R^1$ is a monovalent radical of formula —$C_qH_{2q}$L in which q is a number ranging from 2 to 8 and L is an optionally quaternized amino group chosen from the following groups:

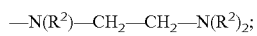

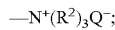

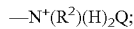

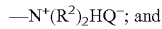

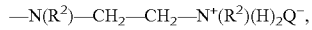

in which $R^2$ can represent a hydrogen, a phenyl, a benzyl or a saturated monovalent hydrocarbon-based radical, for example a $C_1$-$C_{20}$ alkyl radical, and $Q^-$ represents a halide ion such as, for example, fluoride, chloride, bromide or iodide.

For example, the amino silicones of formula (XVI) can be chosen from the compounds of formula (XVII):

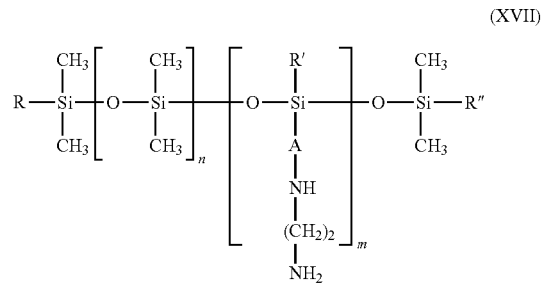

(XVII)

in which R, R' and R", which may be identical or different, represent a $C_1$-$C_4$ alkyl radical, such as $CH_3$; a $C_1$-$C_4$ alkoxy radical, such as methoxy; or OH; A represents a linear or branched, $C_3$-$C_8$ and for example $C_3$-$C_6$ alkylene radical; m and n are integers dependent on the molecular weight and whose sum ranges from 1 to 2000.

According to at least one embodiment, R, R' and R", which may be identical or different, represent a $C_1$-$C_4$ alkyl or hydroxyl radical, A represents a $C_3$ alkylene radical and m and n are such that the weight-average molecular mass of the compound ranges from 5000 to 500,000. Compounds of this type, for example, are referred to in the CTFA dictionary as Amodimethicones.

According to at least one embodiment, R, R' and R", which may be identical or different, represent a $C_1$-$C_4$ alkoxy or hydroxyl radical, at least one of R and R" is an alkoxy radical and A represents a $C_3$ alkylene radical. The hydroxyl:alkoxy mole ratio, for example, ranges from 0.2:1 to 0.4:1 and such as equal to 0.3:1. Moreover, m and n are such that the weight-average molecular mass of the compound ranges from 2000 to 1,000,000. For example, n ranges from 0 to 999 and m ranges from 1 to 1000, the sum of n and m being from 1 to 1000.

In this category of compounds, mention may be made, inter alia, of the product BELSIL® ADM 652 sold by Wacker.

According to at least one embodiment, R and R", which are different, represent a $C_1$-$C_4$ alkoxy or hydroxyl radical, at least one of R and R" is an alkoxy radical, R' represents a methyl radical and A represents a $C_3$ alkylene radical. The hydroxyl:alkoxy mole ratio, for example, ranges from 1:0.8 to 1:1.1 and is, in at least one embodiment for example equal to 1:0.95. Moreover, m and n are such that the weight-average molecular mass of the compound ranges from 2000 to 200,000. For example, n ranges from 0 to 999 and m ranges from 1 to 1000, the sum of n and m being from 1 to 1000.

For example, mention may be made of the product FLUID WR® 1300 sold by Wacker.

As disclosed herein, the molecular mass of these silicones can be determined by gel permeation chromatography (ambient temperature, polystyrene standard; μ styragem columns; eluent THF; flow rate 1 mm/m; 200 μl of a solution containing 0.5% by weight of silicone are injected into THF and detection is performed by UV refractometry).

Examples of formula (XVI) can be the polymer known in the CTFA dictionary as Trimethylsilyl Amodimethicone, of formula (XIX):

$$(CH_3)_3-SiO-\left[\begin{array}{c}CH_3\\|\\Si-O\\|\\CH_3\end{array}\right]_n-\left[\begin{array}{c}CH_3\\|\\Si-O\\|\\CH_2\\|\\CHCH_3\\|\\CH_2\\|\\NH\\|\\(CH_2)_2\\|\\NH_2\end{array}\right]_m-Si(CH_3)_3 \quad (XIX)$$

in which n and m have the meanings given above in accordance with formula (XVI).

Such compounds are described, for example, in patent application EP-A-95238; a compound of formula (XIX) is sold, for example, under the name Q2-8220 by the company OSI.

(b) compounds of formula (XX):

$$R^4-CH_2-CHOH-CH_2-N^+(R^3)_3 \quad Q^- \quad (XX)$$

$$R^3-\underset{\underset{R^3}{|}}{\overset{\overset{R^3}{|}}{Si}}-O-\left[\underset{\underset{R^3}{|}}{\overset{\overset{R^3}{|}}{Si}}-O\right]_r-\left[\underset{\underset{R^3}{|}}{\overset{\overset{R^3}{|}}{Si}}-O\right]_s-\underset{\underset{R^3}{|}}{\overset{\overset{R^3}{|}}{Si}}-R^3$$

in which:

$R^3$, which may be identical or different, represents a monovalent $C_1$-$C_{18}$ hydrocarbon-based radical, and for example a $C_1$-$C_{18}$ alkyl or $C_2$-$C_{18}$ alkenyl radical, for example methyl;

$R^4$ represents a divalent hydrocarbon-based radical, such as a $C_1$-$C_{18}$ alkylene radical or a divalent $C_1$-$C_{18}$, and for example $C_1$-$C_8$, alkyleneoxy radical;

$Q^-$ is a halide ion, such as chloride;

r represents an average statistical value ranging from 2 to 20 and such as from 2 to 8;

s represents an average statistical value ranging from 20 to 200 and such as from 20 to 50.

Such compounds are described, for example, in U.S. Pat. No. 4,185,087.

A compound falling within this class is the product sold by the company Union Carbide under the name UCAR SILICONE ALE 56.

(c) quaternary ammonium silicones of formula (XXI):

$$R_8-\underset{\underset{R_7}{|}}{\overset{\overset{R_7}{|}}{N^+}}-CH_2-\overset{\overset{OH}{|}}{CH}-CH_2-R_6-\left[\underset{\underset{R_7}{|}}{\overset{\overset{R_7}{|}}{Si}}-O\right]_r-\underset{\underset{R_7}{|}}{\overset{\overset{R_7}{|}}{Si}}-R_6-CH_2-CHOH-CH_2-\underset{\underset{R_7}{|}}{\overset{\overset{R_7}{|}}{N^+}}-R_8 \quad 2X^- \quad (XXI)$$

in which:

$R_7$, which may be identical or different, represents a monovalent hydrocarbon-based radical comprising from 1 to 18 carbon atoms, and for example a $C_1$-$C_{18}$ alkyl radical such as methyl, a $C_2$-$C_{18}$ alkenyl radical or a ring comprising 5 or 6 carbon atoms;

$R_6$ represents a divalent hydrocarbon-based radical, for example, a $C_1$-$C_{18}$ alkylene radical or a divalent $C_1$-$C_{18}$, for example, $C_1$-$C_8$, alkyleneoxy radical linked to the Si via an Si—C bond;

$R_8$, which may be identical or different, represents a hydrogen, or a monovalent hydrocarbon-based radical comprising from 1 to 18 carbon atoms, and such as a $C_1$-$C_{18}$ alkyl radical, a $C_2$-$C_{18}$ alkenyl radical or a —$R_6$—$NHCOR_7$ radical;

$X^-$ is an anion such as a halide ion, further such as chloride, or an organic acid salt (acetate, etc.);

r represents an average statistical value ranging from 2 to 200 and such as from 5 to 100.

These silicones are described, for example, in patent application EP-A 0 530 974.

(d) the amino silicones of formula (XXII):

$$\underset{\underset{\underset{\underset{NH_2}{|}}{(C_mH_{2m})}}{\underset{|}{NH}}}{\underset{|}{Si}}-\left[O-\left[\underset{\underset{R_2}{|}}{\overset{\overset{R_1}{|}}{Si}}-O\right]_x-\underset{\underset{R_4}{|}}{\overset{\overset{R_3}{|}}{Si}}-R_5\right]_3 \quad (XXII)$$

in which:

$R_1$, $R_2$, $R_3$ and $R_4$, which may be identical or different, represent a $C_1$-$C_4$ alkyl radical or a phenyl group, $R_5$ represents a $C_1$-$C_4$ alkyl radical or a hydroxyl group, n is an integer ranging from 1 to 5, m is an integer ranging from 1 to 5, and in which x is chosen such that the amine number ranges from 0.01 and 1 meq/g.

According to at least one embodiment, the amino silicones used in the compositions disclosed herein do not comprise any quaternary ammonium groups.

The term "cosmetically acceptable medium" means a medium that is compatible with keratin fibers, such as the hair.

The cosmetically acceptable medium comprises water or a mixture of water and at least one cosmetically acceptable solvent chosen from $C_1$-$C_4$ lower alcohols, such as ethanol, isopropanol, tert-butanol and n-butanol; and polyols such as glycerol, propylene glycol and polyethylene glycols.

The pH of the compositions disclosed herein may range from 3 to 11, such as from 5 to 10 and further such as from 7 to 10.

The composition disclosed herein may also comprise at least one standard additive that may be well known in the art, for example, chosen from natural synthetic thickeners and viscosity regulators; $C_{12}$-$C_{30}$ fatty alcohols; ceramides; fatty esters such as isopropyl myristate, myristyl myristate, cetyl palmitate and stearyl stearate; mineral, plant and synthetic oils such as α-olefins and avocado oil, rapeseed oil, apricot kernel oil, camellina oil and liquid petroleum jelly; vitamins and provitamins; cationic and amphoteric polymers; pH stabilizers, preserving agents; and dyes.

The thickener(s) may be chosen from cellulose-based thickeners, for example hydroxyethylcellulose, hydroxypropylcellulose and carboxymethylcellulose, guar gum and derivatives thereof, for example the hydroxypropyl guar sold by the company Rhodia under the reference JAGUAR HP 105, gums of microbial origin, such as xanthan gum and scleroglucan gum, synthetic thickeners such as crosslinked acrylic acid and acrylamidopropanesulfonic acid homopolymers, for example Carbomer, nonionic, anionic, cationic and amphoteric associative polymers, such as the polymers sold under the names PEMULEN TR1 and TR2 by the company Goodrich, SALCARE SC90 by the company Ciba, ACULYN 22, 28, 33, 44 or 46 by the company Rohm & Haas, and ELFACOS T210 and T212 by the company Akzo.

A person skilled in the art will take care to select the optional additive(s) and the amount thereof such that they do not harm the properties of the compositions of the present disclosure.

The at least one additive may be present in the composition disclosed herein in a total amount ranging from 0 to 20% by weight relative to the total weight of the composition.

According to at least one embodiment, the cosmetic compositions disclosed herein are transparent or translucent, e.g., these compositions allow a transmittance at 600 nm of greater than 85%, such as greater than 90% and further such as greater than 94%.

The compositions disclosed herein may be used as shampoos for washing and conditioning the hair, and they are, for example, applied to wet hair in amounts that are effective for washing them, and the lather generated by massaging or frictioning with the hands may then be removed, after an optional leave-on time, by rinsing with water, the operation possibly being repeated at least one time.

Provided also is a cosmetic process for treating keratin fibers, such as the hair, comprising applying an effective amount of a composition as described above to the fibers, and optionally rinsing out the composition after an optional leave-on time.

For example, the cosmetic process for treating keratin fibers is a process of washing and conditioning the keratin fibers, such as the hair.

The example that follows serves to illustrate the present disclosure without limiting the scope thereof.

EXAMPLE

Composition A according to the disclosure was prepared from the ingredients indicated in the table below, the amounts of which were expressed as weight percentages of product in the given form, relative to the total weight of the composition.

| Composition | A according to the disclosure |
|---|---|
| Lactic acid | 0.27 |
| Mixture of chloro-5-methyl-2-isothiazolin-4-one-3/methylisothiazolin-4-one-3/magnesium chloride | 0.1 |

-continued

| Composition | A according to the disclosure |
|---|---|
| and nitrate in aqueous solution[1] | |
| Polyethoxylated (55 EO) propylene glycol oleate and propylene glycol oleate as a water-glycol solution[2] | 0.6 |
| Hydroxyethylcellulose quaternized with 2,3-epoxypropyltrimethylammonium chloride at 95% AM[3] | 0.6 |
| Polydimethylsiloxane comprising aminoethyl aminoisobutyl and trimethylsiloxy groups[4] | 1 |
| 3-Aminopropyltriethoxysilane[5] | 0.75 |
| Cocoylbetaine at 30% AM in aqueous solution[6] | 17 |
| Oxyethylenated (20 OE) and oxypropylenated (5 OP) cetyl alcohol[7] | 0.5 |
| Lauryl ether carboxylic acid (4.5 OE) at 90% active material in water[8] | 1 |
| Coconut acid monoisopropanolamide at 94.5% active material[9] | 0.85 |
| Sodium lauryl ether sulfate (2.2 OE) as an aqueous solution (70% AM)[10] | 16 |
| Citric acid or sodium hydroxide | qs pH 9 |
| Fragrance | 0.5 |
| Deionized water | qs 100 g |

[1] sold under the trade name KATHON CG by the company Rohm & Haas
[2] sold under the trade name ANTIL 141 LIQUID by the company Evonik Goldschmidt
[3] sold under the trade name POLYQUAT 400 KC by the company KCI
[4] sold under the trade name DC 28566 AMINO FLUID by the company Dow Corning
[5] sold under the name XIAMETER OFS EO11 SILANE by the company Dow Corning
[6] sold under the name MIRATAINER BB/FLA by the company Rhodia
[7] sold under the name PROCETYL AWS-LQ by the company Croda
[8] sold under the name AKYPO RLM 45 CA by the company Kao
[9] sold under the name EMPILAN CIS by the company Huntsman
[10] sold under the name TEXAPON AOS 225UP by the company Cognis A composition that was clear and stable over time was obtained.

When applied as a shampoo, composition afforded satisfactory styling effects: for example, this composition gave satisfactory results in terms of the hair body, volume and/or soft feel.

What is claimed is:

1. A cosmetic composition for washing and conditioning keratin fibers, comprising, in a cosmetically acceptable medium:

at least one organosilicon compound chosen from compounds of formula (III):

(III)

wherein:
the radicals R, which may be identical or different, are chosen from $C_6$ alkyl radicals, and
n is an integer ranging from 1 to 6;
(ii) at least one anionic surfactant chosen from sulfate and sulfonate anionic surfactants;
(iii) at least one carboxylic anionic surfactant other than the at least one anionic surfactant of (ii) chosen from compounds of formula (IV):

R$_1$—(OC$_2$H$_4$)$_n$—OCH$_2$COOA (IV)

wherein:
R$_1$ represents a (C$_{12}$-C$_{14}$)alkyl, cocoyl or oleyl radical; a nonylphenyl or octylphenyl radical, and
A represents hydrogen or Na$^+$, and
n ranges from 2 to 20;

(iv) at least one amphoteric surfactant; and
(v) at least one carboxylic organic acid.

2. The cosmetic composition according to claim 1, wherein in formula (III), n is an integer ranging from 2 to 4.

3. The cosmetic composition according to claim 1, wherein the at least one anionic surfactant chosen from sulfate and sulfonate anionic surfactants is chosen from sodium, triethanolamine, magnesium and ammonium ($C_{12}$-$C_{14}$)alkyl sulfates, sodium, ammonium and magnesium ($C_{12}$-$C_{14}$)alkyl ether sulfates, sodium cocoyl isethionate and methyl acyl taurates.

4. The cosmetic composition according to claim 1, wherein the at least one anionic surfactant chosen from sulfate and sulfonate anionic surfactants is chosen from sodium ($C_{12}$-$C_{14}$)alkyl ether sulfates.

5. The cosmetic composition according to claim 1, wherein in formula (IV), n is an integer ranging from 2 to 10.

6. The cosmetic composition according to claim 1, wherein A is $Na^+$.

7. The cosmetic composition according to claim 1, wherein the at least one amphoteric surfactant is chosen from ($C_{8-20}$ alkyl)betaines and ($C_{8-20}$ alkyl)amido($C_{6-8}$ alkyl)betaines.

8. The cosmetic composition according to claim 1, further comprising at least one cationic polymer and/or at least one silicone.

9. A cosmetic process for treating keratin fibers comprising,
applying to the keratin fibers at least one cosmetic composition, and optionally rinsing out the at least one cosmetic composition after an optional leave-on time,
wherein the at least one cosmetic composition comprises, in a cosmetically acceptable medium:
(i) at least one organosilicon compound chosen from compounds of formula (III):

(III)

wherein:
the radicals R, which may be identical or different, are chosen from $C_1$-$C_6$ alkyl radicals, and
n is an integer ranging from 1 to 6;
(ii) at least one anionic surfactant chosen from sulfate and sulfonate anionic surfactants;
(iii) at least one carboxylic anionic surfactant other than the at least one anionic surfactant of (ii) chosen from compounds of formula (IV):

$$R_1\text{---}(OC_2H_4)_n\text{---}OCH_2COOA \quad \text{(IV)}$$

wherein:
$R_1$ represents a ($C_{12}$-$C_{14}$)alkyl, cocoyl or oleyl radical; a nonylphenyl or octylphenyl radical, and
A represents hydrogen or $Na^+$, and
n ranges from 2 to 20;
(iv) at least one amphoteric surfactant; and
(v) at least one carboxylic organic acid.

* * * * *

UNITED STATES PATENT AND TRADEMARK OFFICE
CERTIFICATE OF CORRECTION

| | | |
|---|---|---|
| PATENT NO. | : 9,248,083 B2 | Page 1 of 1 |
| APPLICATION NO. | : 12/977458 | |
| DATED | : February 2, 2016 | |
| INVENTOR(S) | : Carine Aires et al. | |

It is certified that error appears in the above-identified patent and that said Letters Patent is hereby corrected as shown below:

In the claims,

Claim 1, Col. 20, line 54, "C6" should be -- C1-C6 --.

Signed and Sealed this
Nineteenth Day of April, 2016

Michelle K. Lee
*Director of the United States Patent and Trademark Office*